United States Patent
Boulanger

(10) Patent No.: US 10,906,912 B2
(45) Date of Patent: *Feb. 2, 2021

(54) PHARMACEUTICAL INTERMEDIATES AND METHODS FOR PREPARING THE SAME

(71) Applicant: William Allen Boulanger, Mahomet, IL (US)

(72) Inventor: William Allen Boulanger, Mahomet, IL (US)

(73) Assignee: King T, LLC, Champaign, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/228,326

(22) Filed: Mar. 28, 2014

(65) Prior Publication Data

US 2014/0213783 A1 Jul. 31, 2014

Related U.S. Application Data

(62) Division of application No. 13/346,815, filed on Jan. 10, 2012, now abandoned.

(51) Int. Cl.
| | |
|---|---|
| *C07D 487/06* | (2006.01) |
| *C07D 487/10* | (2006.01) |
| *C07D 487/18* | (2006.01) |
| *C07D 487/04* | (2006.01) |

(52) U.S. Cl.
CPC ......... *C07D 487/06* (2013.01); *C07D 487/04* (2013.01); *C07D 487/10* (2013.01); *C07D 487/18* (2013.01)

(58) Field of Classification Search
CPC .................. C07D 487/04; C07D 487/06
See application file for complete search history.

(56) References Cited

U.S. PATENT DOCUMENTS

| | | | |
|---|---|---|---|
| 3,478,051 A | 11/1969 | Houlihan et al. | |
| 3,525,750 A | 8/1970 | Renner | |
| 3,681,362 A | 8/1972 | Nagata et al. | |
| 4,122,082 A | 10/1978 | Wright et al. | |
| 4,146,643 A | 3/1979 | Pfaffli | |
| 4,154,943 A | 5/1979 | Kuehne | |
| 4,220,774 A | 9/1980 | Kuehne | |
| 4,267,330 A | 5/1981 | Kuehne | |
| 4,283,536 A | 8/1981 | Kuehne | |
| 4,362,739 A | 12/1982 | Kuehne | |
| 4,428,880 A | 1/1984 | Kuehne | |
| 4,490,378 A | 12/1984 | Dancsi et al. | |
| 4,499,096 A | 2/1985 | Lotsof | |
| 4,558,053 A | 12/1985 | Rolski et al. | |
| 4,587,243 A | 5/1986 | Lotsof | |
| 4,596,676 A | 6/1986 | Cullinan | |
| 4,746,665 A | 5/1988 | Szantay | |
| 4,769,453 A | 9/1988 | Potier et al. | |
| 4,841,045 A | 6/1989 | Kuehne | |
| 4,897,477 A | 1/1990 | Kuehne | |
| 4,935,509 A | 6/1990 | Kuehne | |
| 4,946,853 A | 8/1990 | Lavielle et al. | |
| 5,095,109 A | 3/1992 | Kuehne | |
| 5,152,994 A | 10/1992 | Lotsof | |
| 5,369,111 A | 11/1994 | Kuehne et al. | |
| 5,654,281 A | 8/1997 | Mayer et al. | |
| 5,863,927 A | 1/1999 | Smith et al. | |
| 5,965,567 A | 10/1999 | Archer et al. | |
| 6,211,360 B1 | 4/2001 | Glick et al. | |
| 6,780,871 B2 | 8/2004 | Glick et al. | |
| 9,399,642 B2 * | 7/2016 | Boulanger | ........... C07D 487/10 |
| 2009/0281134 A1 | 11/2009 | Glick et al. | |
| 2010/0152200 A1 | 6/2010 | Miller et al. | |
| 2013/0178618 A1 * | 7/2013 | Boulanger | ........... C07D 487/06 540/479 |

FOREIGN PATENT DOCUMENTS

| | | | | |
|---|---|---|---|---|
| WO | 2000038677 | * | 7/2000 | ........... A61K 31/415 |
| WO | 2002/24700 | * | 5/2002 | ........... C07D 487/04 |

OTHER PUBLICATIONS

Acheson. Heterocyclic Compounds, 1965, 2630-33.*
Keuhne. Journal of Organic Chemistry, 1978, 43(19), 3705-10.*
Zheng, Tetrahedron Letters, 2005, 46(20), 3529-32.
Bandarage. Tetrahedron, 1999, 55, 9405-24.
Bornmann. Journal of Organic Chemistry, 1992, 57, 1752-60.
Bandarage. Current Medicinal Chemistry-Central Nervous System Agents, 2001, 1, 113-23.
Greene. Protective Groups in Organic Synthesis, 1999, pp. 494-503 and 574-581.
Office Action for U.S. Appl. No. 13/346,815 dated Apr. 23, 2014.
Office Action for U.S. Appl. No. 13/346,815 dated Aug. 25, 2016.
Office Action for U.S. Appl. No. 13/346,815 dated Sep. 5, 2013.
Office Action for U.S. Appl. No. 13/346,815 dated Sep. 30, 2014.
Office Action for U.S. Appl. No. 14/228,303 dated Oct. 20, 2015.
Office Action for U.S. Appl. No. 14/228,316 dated Oct. 28, 2015.

* cited by examiner

*Primary Examiner* — Noble E Jarrell
(74) *Attorney, Agent, or Firm* — King & Partners, PLC

(57) ABSTRACT

A pharmaceutical intermediate including a first indole moiety which is associated with an optionally carboxylated hexahydroazepino moiety, an optionally carboxylated azonane moiety, or a second, optionally carboxylated indole moiety, having an alkyl, allyl, phenylallyl, cinnamyl, alkenyl, and/or alkyl-alkenyl substituent pendant from a nitrogen atom of the same.

3 Claims, No Drawings

PHARMACEUTICAL INTERMEDIATES AND METHODS FOR PREPARING THE SAME

CROSS-REFERENCE TO RELATED APPLICATIONS

This application is a divisional of U.S. application Ser. No. 13/346,815, filed Jan. 10, 2012, entitled "Novel Pharmaceutical Intermediates and Methods for Preparing the Same" which is hereby incorporated herein by reference in its entirety, including all references cited therein.

BACKGROUND OF THE INVENTION

1. Field of the Invention

The present invention relates in general to novel pharmaceutical intermediates and, more particularly, to novel indole derived pharmaceutical intermediates and methods for preparing the same. The novel compounds of the present invention are preferably suitable for participation in direct or multi-step convergent syntheses with other compounds including, but not limited to, aldehyde derived pharmaceutical intermediates, etcetera.

2. Background Art

The commercial development of novel pharmaceutical compounds is, often times, replete with arduous problems relative to transitioning from research and development scale to plant scale synthesis. A plurality of complex issues, including reagent cost, reaction yield, reaction time, competitive side reactions, product isolation and/or purification, disposal of toxic waste and/or byproducts remain largely problematic for the scale-up of most pharmaceutical endeavors.

Problems associated with preparing novel pharmaceutical compounds can become exponentially difficult when, for example, intermediates comprise delicate compounds where one or more atoms, functional groups, and/or moieties need to be associated with a protecting group during one or more steps of a synthesis. For example, hexahydroazepinoindolecarboxylate intermediates comprise a nitrogen atom on the heptacyclic moiety which is commonly protected with a benzyl group during multi-step synthesis. However, obtaining a final product normally necessitates removing the benzyl group which is a great liability—especially at commercial scale. Notably, copious quantities of expensive catalyst (e.g., palladium) must be used to remove the benzyl group. To make matters more complex, reaction conditions are such that significant side reactions occur, thereby: (1) adversely affecting the net yield; (2) materially increasing product cost; and (3) substantially increasing isolation and purification difficulties. Notably, the above-identified problems are very difficult to solve because other types of classical protection of the nitrogen atom—such as carboxybenzyl groups or amides can prevent a desired reaction sequence altogether.

While indole derived pharmaceutical intermediates have been the subject of recent study, to the best of Applicant's knowledge, no such intermediates have been identified today that facilitate practical transition from research and development scale to commercial, plant scale synthesis.

It is therefore an object of the present invention to provide novel indole derived pharmaceutical intermediates and their syntheses which will partially and/or fully remedy the above-identified issues associated with the commercialized development of pharmaceuticals.

These and other objects of the present invention will become apparent in light of the present specification, claims, chemical structures, chemical formulae, and drawings.

SUMMARY OF THE INVENTION

In one embodiment the present invention is directed to a pharmaceutical intermediate which comprises the structure of formula I:

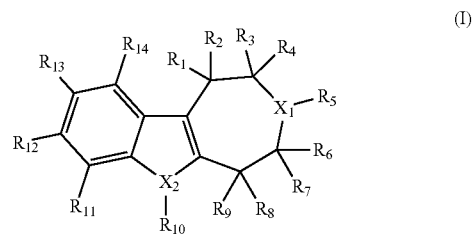

wherein: $R_1$-$R_4$, $R_6$-$R_8$, and $R_{10}$-$R_{14}$ are each independently selected from the group consisting of H; OH; and an alkyl, cycloalkyl, polycycloalkyl, heterocycloalkyl, aryl, alkaryl, aralkyl, alkoxy, alkanoyl, aroyl, alkenyl, and/or alkyl-alkenyl group containing approximately 1 to approximately 25 carbon atom(s); $R_5$ is selected from the group consisting of an alkyl (e.g., methyl, ethyl, t-butyl, neopentyl, adamantyl, etcetera), allyl, phenylallyl, cinnamyl, alkenyl, and/or alkyl-alkenyl group containing approximately 1 to approximately 25 carbon atom(s); $R_9$ is selected from the group consisting of H; OH; and an alcohol, ether, ester, amide, hydrazide, cyanide, and/or ketone group containing approximately 1 to approximately 25 carbon atom(s); and $X_1$-$X_2$ are each independently selected from the group consisting of N, O, and S.

In a preferred embodiment of the present invention, the pharmaceutical intermediate comprises the structure of formula II:

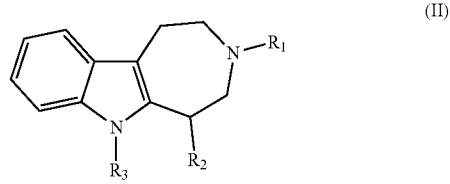

wherein: $R_1$ is selected from the group consisting of an alkyl, allyl, phenylallyl, cinnamyl, alkenyl, and/or alkyl-alkenyl group containing approximately 1 to approximately 25 carbon atom(s); $R_2$ is selected from the group consisting of H; OH; and an alcohol, ether, ester, amide, hydrazide, cyanide, and/or ketone group containing approximately 1 to approximately 25 carbon atom(s); and $R_3$ is selected from the group consisting of H; OH; and an alkyl, cycloalkyl, polycycloalkyl, heterocycloalkyl, aryl, alkaryl, aralkyl, alkoxy, alkanoyl, aroyl, alkenyl, and/or alkyl-alkenyl group containing approximately 1 to approximately 25 carbon atom(s).

In another preferred embodiment of the present invention, the pharmaceutical intermediate comprises the structure of formula III:

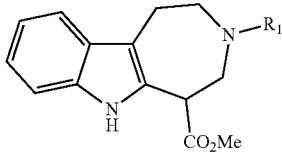
(III)

wherein R₁ is selected from the group consisting of an alkyl, allyl, phenylallyl, cinnamyl, alkenyl, and/or alkyl-alkenyl group containing approximately 1 to approximately 25 carbon atom(s).

In yet another preferred embodiment of the present invention, the pharmaceutical intermediate comprises the structure of formula IV:

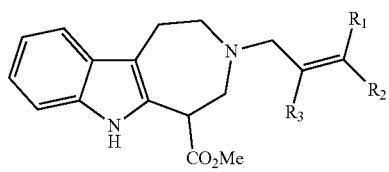
(IV)

wherein R₁-R₃ are each independently selected from the group consisting of H, CH₃, and C₆H₅.

In this embodiment of the present invention, exemplary examples of pharmaceutical intermediates may comprise
methyl 3-allyl-1,2,3,4,5,6-hexahydroazepino[4,5-b]indole-5-carboxylate,
methyl 3-cinnamyl-1,2,3,4,5,6-hexahydroazepino[4,5-b]indole-5-carboxylate,
methyl 3-(2-phenylallyl)-1,2,3,4,5,6-hexahydroazepino[4,5-b]indole-5-carboxylate,
methyl 3-(3-methylbut-2-en-1-yl)-1,2,3,4,5,6-hexahydroazepino[4,5-b]indole-5-carboxylate, and combinations thereof.

The present invention is also directed to a pharmaceutical intermediate which comprises the structure of formula V:

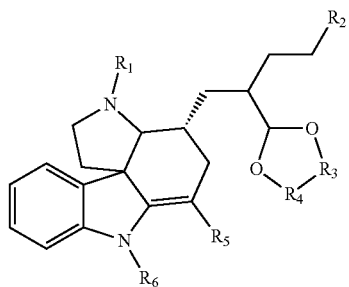
(V)

wherein: R₁ is selected from the group consisting of an alkyl, allyl, phenylallyl, cinnamyl, alkenyl, and/or alkyl-alkenyl group containing approximately 1 to approximately 25 carbon atom(s); R₂-R₄ and R₆ are each independently selected from the group consisting of H; OH; and an alkyl, cycloalkyl, polycycloalkyl, heterocycloalkyl, aryl, alkaryl, aralkyl, alkoxy, alkanoyl, aroyl, and/or alkyl-alkenyl group containing approximately 1 to approximately 25 carbon atom(s); and R₅ is selected from the group consisting of H; OH; and an alcohol, ether, ester, amide, hydrazide, cyanide, and/or ketone group containing approximately 1 to approximately 25 carbon atom(s).

In a preferred embodiment of the present invention, the pharmaceutical intermediate comprises the structure of formula VI:

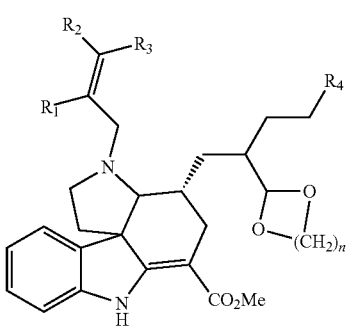
(VI)

wherein: R₁-R₃ are each independently selected from the group consisting of H, CH₃, and C₆H₅; R₄ is selected from the group consisting of an alkyl, cycloalkyl, polycycloalkyl, heterocycloalkyl, aryl, alkaryl, aralkyl, alkoxy, alkanoyl, aroyl, alkenyl, and/or alkyl-alkenyl group containing approximately 1 to approximately 25 carbon atom(s); and n is an integer ranging from approximately 2 to approximately 5.

In this embodiment of the present invention, exemplary examples of pharmaceutical intermediates may comprise the structures of formulae VII and/or VIII, namely:

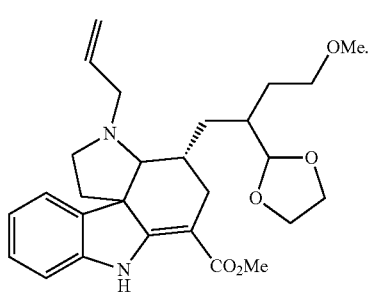
(VII)

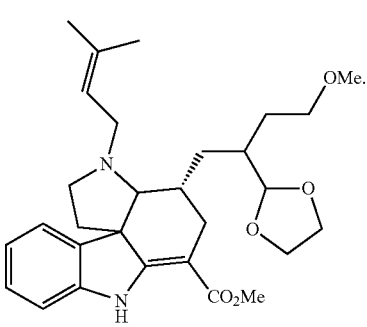
(VIII)

The present invention is further directed to a pharmaceutical intermediate which comprises the structure of formula IX:

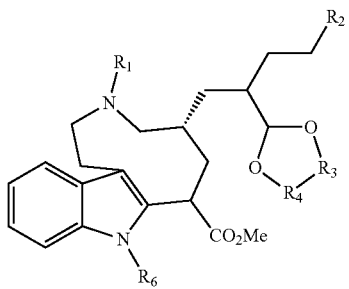

(IX)

wherein: $R_1$ is selected from the group consisting of an alkyl, allyl, phenylallyl, cinnamyl, alkenyl, and/or alkyl-alkenyl group containing approximately 1 to approximately 25 carbon atom(s); $R_2$-$R_4$ and $R_6$ are each independently selected from the group consisting of H; OH; and an alkyl, cycloalkyl, polycycloalkyl, heterocycloalkyl, aryl, alkaryl, aralkyl, alkoxy, alkanoyl, aroyl, alkenyl, and/or alkyl-alkenyl group containing approximately 1 to approximately 25 carbon atom(s); and $R_5$ is selected from the group consisting of H; OH; and an alcohol, ether, ester, amide, hydrazide, cyanide, and/or ketone group containing approximately 1 to approximately 25 carbon atom(s).

In a preferred embodiment of the present invention, the pharmaceutical intermediate comprises the structure of formula X:

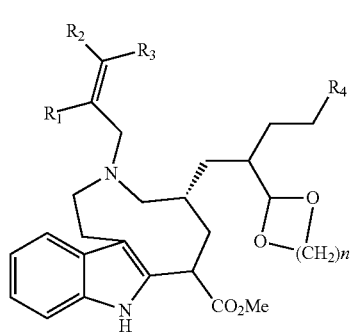

(X)

wherein: $R_1$-$R_3$ are each independently selected from the group consisting of H, $CH_3$, and $C_6H_5$; $R_4$ is selected from the group consisting of an alkyl, cycloalkyl, polycycloalkyl, heterocycloalkyl, aryl, alkaryl, aralkyl, alkoxy, alkanoyl, aroyl, and/or alkyl-alkenyl group containing approximately 1 to approximately 25 carbon atom(s); and n is an integer ranging from approximately 2 to approximately 5.

In this embodiment of the present invention, exemplary examples of pharmaceutical intermediates may comprise the structures of formulae XI and/or XII, namely:

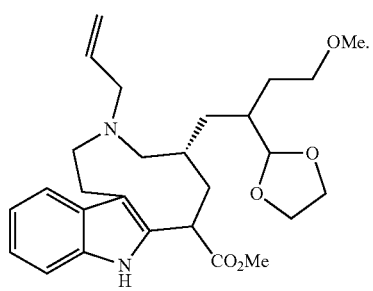

(XI)

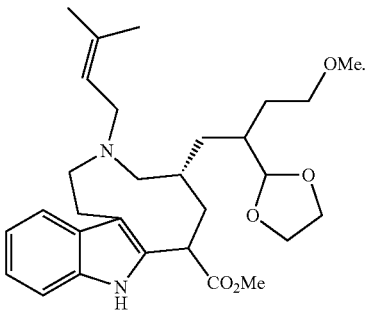

(XII)

DETAILED DESCRIPTION OF THE INVENTION

While this invention is susceptible of embodiment in many different forms, there is shown in the structural formulas and described herein in detail several specific embodiments with the understanding that the present disclosure is to be considered as an exemplification of the principles of the invention and is not intended to limit the invention to the embodiments illustrated. It will be understood that the structural formulas disclosed herein are intended to comprise all stereochemcial configurations regardless of graphical representations.

In accordance with the present invention, and as is shown herein below, novel indole derived pharmaceutical intermediates have been discovered which are surprisingly effective and efficient in direct or multi-step convergent syntheses with other compounds including, but not limited to, aldehyde derived pharmaceutical intermediates, etcetera. By way of broad characterization, the indole derived pharmaceutical intermediates preferably include an indole moiety which is associated with an optionally carboxylated hexahydroazepino moiety, (e.g., formulae I-IV), an optionally carboxylated azonane moiety, (e.g., formulae IX-XII) or an additional optionally carboxylated indole moiety (e.g., formulae V-VIII) moiety, having an alkyl (e.g., methyl, ethyl, t-butyl, neopentyl, adamantyl, etcetera), allyl, phenylallyl, cinnamyl, alkenyl, and/or alkyl-alkenyl substituent pendant from the nitrogen atom of the same.

In a first embodiment of the present invention, a pharmaceutical intermediate is disclosed which comprises, consists, and/or consists essentially of the structure of formula I:

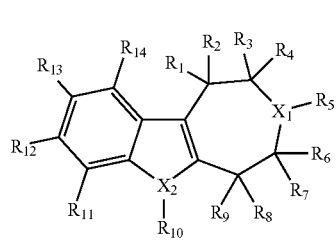

(I)

wherein: $R_1$-$R_4$, $R_6$-$R_8$, and $R_{10}$-$R_{14}$ are each independently selected from the group consisting of H; OH; and an alkyl, cycloalkyl, polycycloalkyl, heterocycloalkyl, aryl, alkaryl, aralkyl, alkoxy, alkanoyl, aroyl, alkenyl, and/or alkyl-alkenyl group containing approximately 1 to approximately 25 carbon atom(s); $R_5$ is selected from the group consisting of an alkyl (e.g., methyl, ethyl, t-butyl), allyl, phenylallyl, cinnamyl, alkenyl, and/or alkyl-alkenyl group containing approximately 1 to approximately 25 carbon atom(s); $R_9$ is selected from the group consisting of H; OH; and an alcohol, ether, ester, amide, hydrazide, cyanide, and/or ketone group containing approximately 1 to approximately 25 carbon atom(s); and $X_1$-$X_2$ are each independently selected from the group consisting of N, O, and S. It will be understood that for the purpose of avoiding prolix, additional suitable examples for a plurality of R groups, including $R_9$ are disclosed in U.S. Pat. No. 6,211,360—which is hereby incorporated herein by reference in its entirety—including all references referred to and/or cited therein.

More preferably, the pharmaceutical intermediate of this embodiment may comprise consist, and/or consist essentially of the structure of formula II:

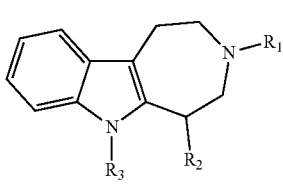

(II)

wherein: $R_1$ is selected from the group consisting of an alkyl, allyl, phenylallyl, cinnamyl, alkenyl, and/or alkyl-alkenyl group containing approximately 1 to approximately 25 carbon atom(s); $R_2$ is selected from the group consisting of H; OH; and an alcohol, ether, ester, amide, hydrazide, cyanide, and/or ketone group containing approximately 1 to approximately 25 carbon atom(s); and $R_3$ is selected from the group consisting of H; OH; and an alkyl, cycloalkyl, polycycloalkyl, heterocycloalkyl, aryl, alkaryl, aralkyl, alkoxy, alkanoyl, aroyl, alkenyl, and/or alkyl-alkenyl group containing approximately 1 to approximately 25 carbon atom(s).

Yet more preferably, the pharmaceutical intermediate of this embodiment may comprise consist, and/or consist essentially of the structure of formula III:

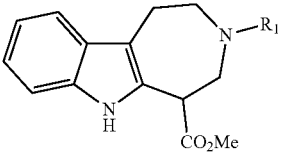

(III)

wherein $R_1$ is selected from the group consisting of an alkyl, allyl, phenylallyl, cinnamyl, alkenyl, and/or alkyl-alkenyl group containing approximately 1 to approximately 25 carbon atom(s).

Additionally, the pharmaceutical intermediate of this embodiment may comprise consist, and/or consist essentially of the structure of formula IV:

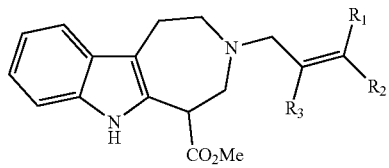

(IV)

wherein: $R_1$-$R_3$ are each independently selected from the group consisting of H, $CH_3$, and $C_6H_5$. Specific examples of indole derived pharmaceutical intermediates include, but are not limited to,
methyl 3-allyl-1,2,3,4,5,6-hexahydroazepino[4,5-b]indole-5-carboxylate,
methyl 3-cinnamyl-1,2,3,4,5,6-hexahydroazepino[4,5-b]indole-5-carboxylate,
methyl 3-(2-phenylallyl)-1,2,3,4,5,6-hexahydroazepino[4,5-b]indole-5-carboxylate,
methyl 3-(3-methylbut-2-en-1-yl)-1,2,3,4,5,6-hexahydroazepino[4,5-b]indole-5-carboxylate, and combinations thereof.

In a second embodiment of the present invention, a pharmaceutical intermediate is disclosed which comprises, consists, and/or consists essentially of the structure of formula V:

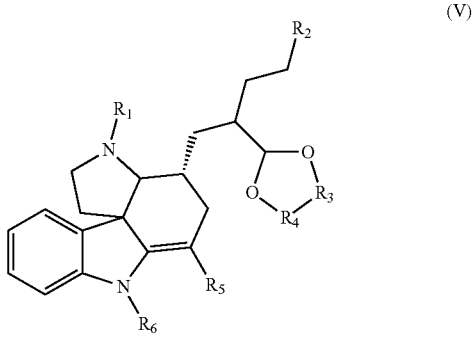

(V)

wherein: $R_1$ is selected from the group consisting of an alkyl, allyl, phenylallyl, cinnamyl, alkenyl, and/or alkyl-alkenyl group containing approximately 1 to approximately 25 carbon atom(s); $R_2$-$R_4$ and $R_6$ are each independently selected from the group consisting of H; OH; and an alkyl, cycloalkyl, polycycloalkyl, heterocycloalkyl, aryl, alkaryl, aralkyl, alkoxy, alkanoyl, aroyl, alkenyl, and/or alkyl-alkenyl group containing approximately 1 to approximately 25 carbon atom(s); and $R_5$ is selected from the group consisting of H; OH; and an alcohol, ether, ester, amide, hydrazide, cyanide, and/or ketone group containing approximately 1 to approximately 25 carbon atom(s).

More preferably, the pharmaceutical intermediate of this embodiment may comprise, consist, and/or consist essentially of the structure of formula VI:

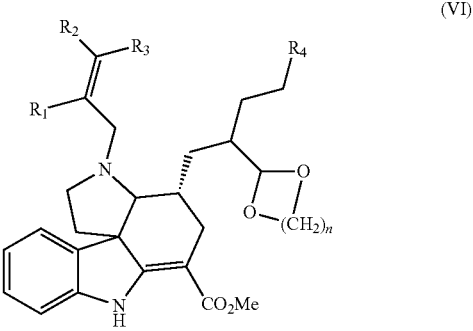

(VI)

wherein: $R_1$-$R_3$ are each independently selected from the group consisting of H, $CH_3$, and $C_6H_5$; $R_4$ is selected from the group consisting of an alkyl, cycloalkyl, polycycloalkyl, heterocycloalkyl, aryl, alkaryl, aralkyl, alkoxy, alkanoyl, aroyl, alkenyl, and/or alkyl-alkenyl group containing approximately 1 to approximately 25 carbon atom(s); and n is an integer ranging from approximately 2 to approximately 5.

Specific examples of this embodiment include, but are not limited to, the structures of formulae VII and/or VIII, namely:

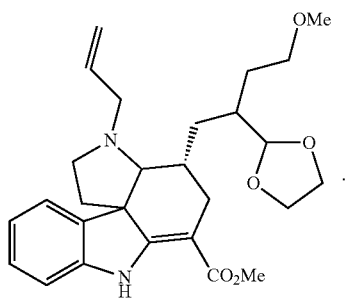

(VII)

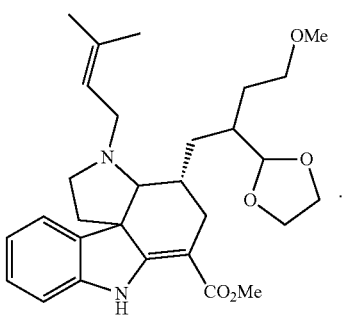

(VIII)

In a third embodiment of the present invention, a pharmaceutical intermediate is disclosed which comprises, consists, and/or consists essentially of the structure of formula IX:

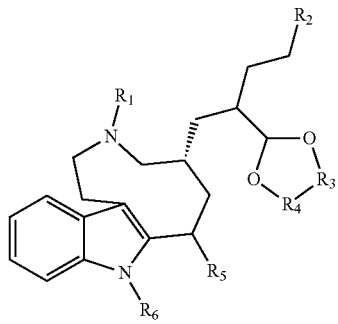

(IX)

wherein: $R_1$ is selected from the group consisting of an alkyl, allyl, phenylallyl, cinnamyl, alkenyl, and/or alkyl-alkenyl group containing approximately 1 to approximately 25 carbon atom(s); $R_2$-$R_4$ and $R_6$ are each independently selected from the group consisting of H; OH; and an alkyl, cycloalkyl, polycycloalkyl, heterocycloalkyl, aryl, alkaryl, aralkyl, alkoxy, alkanoyl, aroyl, alkenyl, and/or alkyl-alkenyl group containing approximately 1 to approximately 25 carbon atom(s); and $R_5$ is selected from the group consisting of H; OH; and an alcohol, ether, ester, amide, hydrazide, cyanide, and/or ketone group containing approximately 1 to approximately 25 carbon atom(s).

More preferably, the pharmaceutical intermediate of this embodiment may comprise, consist, and/or consist essentially of the structure of formula X:

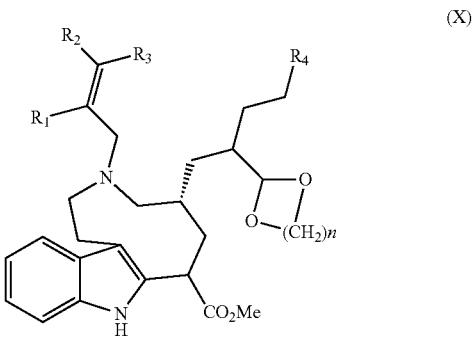

(X)

wherein: $R_1$-$R_3$ are each independently selected from the group consisting of H, $CH_3$, and $C_6H_5$; $R_4$ is selected from the group consisting of an alkyl, cycloalkyl, polycycloalkyl, heterocycloalkyl, aryl, alkaryl, aralkyl, alkoxy, alkanoyl, aroyl, alkenyl, and/or alkyl-alkenyl group containing approximately 1 to approximately 25 carbon atom(s); and n is an integer ranging from approximately 2 to approximately 5.

Specific examples of this embodiment include, but are not limited to, the structures of formulae XI and/or XII, namely:

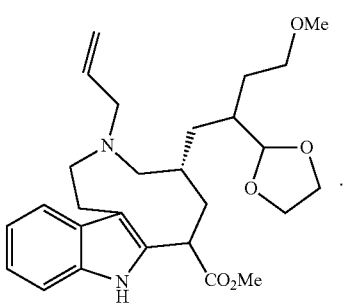

(XI)

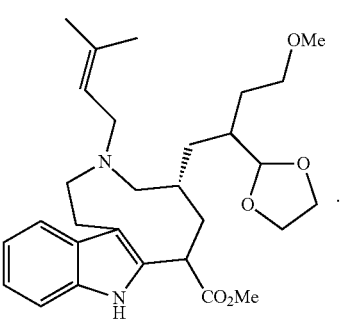

(XII)

The invention is further described by the following examples.

It will be understood that, unless otherwise specified, the chemical reagents provided herein below, or their precursors, are available from common commercial chemical vendors, such as Sigma-Aldrich Chemical Co., of St. Louis, Mo.

Example I

Synthesis of methyl 3-allyl-1,2,3,4,5,6-hexahydroazepino[4,5-b]indole-5-carboxylate

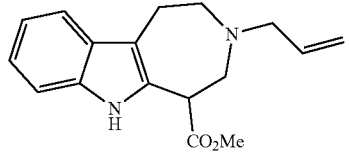 [SMILES: C=CCN1CCc2c([nH]c3ccccc23)C(C(=O)OC)C1]

A 72 L three-necked mechanically stirred round bottomed flask was set up with a reflux condenser. To the flask was charged dry tetrahydrofuran (10 L), and methyl 1,2,3,4,5,6-hexahydroazepino[4,5-b]indole-5-carboxylate (800 g, 3.27 mol). The mixture was stirred, and tetrabutylammonium bromide (21.1 g, 0.06 mol), anhydrous potassium carbonate (1.13 kg, 8.8 mol), and allyl bromide (29.7 mL, 396 g, 3.27 mol) were added sequentially in one lot each. After addition, the mixture was stirred at about 20° C. for 2.5 days. The mixture was diluted with (10 L) hexanes, filtered, and transferred to a separatory funnel. The solution was washed with water (2 L), saturated sodium chloride (1 L), dried over sodium sulfate, filtered, then concentrated to a dark green-brown oil (770 g), methyl 3-allyl-1,2,3,4,5,6-hexahydroazepino[4,5-b]indole-5-carboxylate, suitably clean to be used in the next synthetic step. Yield=83%. TLC (EtOH/CH$_2$Cl$_2$, 1:9): R$_f$=0.7; $^1$H NMR (400 MHz, CDCl$_3$): δ 2.79-2.86 (m, 1H), 2.90-3.09 (m, 4H), 3.28-3.43 (m, 3H), 3.78 (s, 3H), 4.02 (dd, J=1.6, 6.8 Hz, 1H), 5.23 (d, J=10.4 Hz, 1H), 5.27 (dd, J=1.4, 17 Hz, 1H), 5.90-6.00 (m, 1H), 7.11-7.19 (m, 2H), 7.29 (d, J=7.6 Hz, 1H), 7.53 (d, J=7.2 Hz, 1H), 8.40 (bs, 1H); $^{13}$C NMR (100 MHz, CDCl$_3$): δ 24.1, 45.4, 52.2, 55.7, 56.9, 61.4, 110.7, 113.8, 117.5, 118.0, 119.2, 121.4, 128.4, 132.1, 134.7, 135.7, 172.5; melting point: 105-108° C. (uncorrected).

Example II

Synthesis of methyl 3-cinnamyl-1,2,3,4,5,6-hexahydroazepino[4,5-b]indole-5-carboxylate

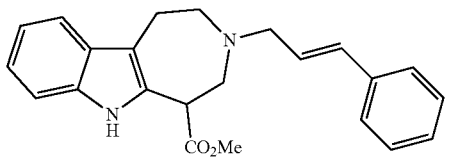 [SMILES: COC(=O)C1CN(C/C=C/c2ccccc2)CCc2c1[nH]c1ccccc21]

A 10 mL vial was charged with azepine (500 mg, 2.05 mmol) and tetrahydrofuran (4.0 mL). Potassium carbonate (565 mg, 4.09 mmol) was added at room temperature in a single portion to the stirred solution followed by addition of cinnamyl bromide (404 mg, 2.05 mmol) as a waxy solid. The reaction mixture was stirred 22 hours then washed into a separatory funnel with hexanes (10 mL), EtOAc (10 mL), and water (10 mL). The layers were partitioned and the organics were washed with water (10 mL), NaCl brine (10 mL), dried over sodium sulfate, and concentrated to an oil. $^1$H NMR (400 MHz, CDCl$_3$): δ 2.85-3.09 (m, 4H), 3.15 (dd, J=4.0, 12.0 Hz, 1H), 3.37-3.54 (m, 3H), 4.10 (dd, J=4.0, 8.0 Hz, 1H), 6.27-6.40 (m, 1H), 6.58 (d, J=16.0 Hz, 1H), 7.06-7.18 (m, 2H), 7.22-7.27 (m, 1H), 7.28-7.44 (m, 5H), 7.50 (d, J=8.0 Hz, 1H), 8.39 (s, 1H).

Example III

Synthesis of methyl 3-(2-phenylallyl)-1,2,3,4,5,6-hexahydroazepino[4,5-b]indole-5-carboxylate

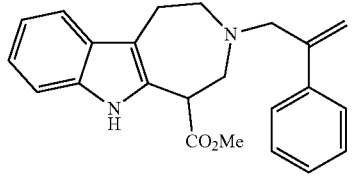 [SMILES: C=C(CN1CCc2c([nH]c3ccccc23)C(C(=O)OC)C1)c1ccccc1]

A 250 mL round bottom flask was charged with azepine (13 g, 53.2 mmol), tetrahydrofuran (100 mL), and stirred as a dark grey suspension. Potassium carbonate (14.9 g, 107.8 mmol) was added in a single portion. A 5:1 mixture of α-bromomethylstyrene and α-methyl-β-bromostyrene (14.3 g, ca. 52.2 mmol α-bromomethylstyrene) was then added at room temperature in a rapid drop wise manner over 2 minutes. The reaction mixture turned from dark grey to light green over 30 hours, at which time the mixture was washed into a separatory funnel with diethyl ether (50 mL), hexanes (50 mL), and water (50 mL). The mixture was partitioned and the aqueous layer was set aside. The organics were washed with water (50 mL) then NaCl brine (50 mL). The combined aqueous washings were extracted with 100 ml EtOAc/Hexanes (1:1) and the combined organics were dried over sodium sulfate then concentrated under reduced pressure. Column chromatography (80 g silica gel, EtOAc/Hexanes eluent) provided the title compound as a yellow oil (18.13 g, 94.5%). TLC (EtOAc/Hexanes, 1:3): R$_f$=0.3; $^1$H NMR (400 MHz, CDCl$_3$): δ 2.76-2.88 (m, 2H), 2.91-3.02 (m, 1H), 3.04-3.10 (m, 1H), 3.15 (dd, J=3.8, 12.0 Hz, 1H), 3.45 (dd, 8.0, 14.0 Hz, 1H), 3.62 (s, 3H), 3.69 (s, 2H), 4.06 (dd, J=2.2, 8.0 Hz, 1H), 5.31 (d, 1.0 Hz, 1H), 5.54 (d, J=1.0 Hz, 1H), 7.06-7.17 (m, 2H), 7.26-7.37 (m, 4H), 7.49 (d, J=8.0 Hz, 1H), 7.54-7.58 (m, 2H), 8.31 (s, 1H); ESI-MS: m/z calculated for C$_{23}$H$_{25}$N$_2$C$_2$, 361.19, found 361.3 [M+H]$^+$.

Example IV

Synthesis of methyl 3-(3-methylbut-2-en-1-yl)-1,2,3,4,5,6-hexahydroazepino[4,5-b]indole-5-carboxylate

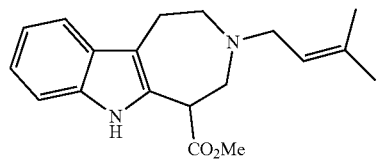 [SMILES: COC(=O)C1CN(CC=C(C)C)CCc2c1[nH]c1ccccc21]

A 250 mL round bottom flask was charged with azepine (10.0 g, 40.93 mmol), tetrahydrofuran (80 mL), and potassium carbonate (11.31 g, 81.83 mmol) at room temperature; in that order. Prenyl bromide (4.73 mL, 40.93 mmol) was added in a rapid drop wise fashion over 2 minutes. The reaction mixture was stirred 21 hours, then additional prenyl bromide (1.0 mL, 8.65 mmol) was added and the reaction stirred an additional 3 hours (24 hours total reaction time) before washing into a separatory funnel with EtOAc (50 mL), hexanes (50 mL), and water (50 mL). The mixture was partitioned and the aqueous layer was set aside. The organics were washed with water (50 mL) then NaCl brine (50 mL).

The combined aqueous washings were extracted with 100 ml EtOAc/Hexanes (1:1) and the combined organics were dried over sodium sulfate then concentrated under reduced pressure. Column chromatography provided the title compound as a yellow oil. TLC (EtOAc/Hexanes, 1:1): $R_f$=0.45; $^1$H NMR (400 MHz, CDCl$_3$): δ 1.68 (s, 3H), 1.77 (s, 3H), 2.79-3.00 (m, 4H), 3.09 (dd, J=3.2, 12.0 Hz, 1H), 3.24-3.35 (m, 3H), 3.78 (s, 3H), 4.08 (dd, J=2.4, 8.0 Hz, 1H), 5.28-5.34 (m, 1H), 7.07-7.17 (m, 2H), 7.30 (d, J=8.0 Hz, 1H), 7.49 (d, J=8.0 Hz, 1H), 8.40 (s, 1H); ESI-MS: m/z calculated for $C_{19}H_{25}N_2O_2$, 313.19, found 313.3 [M+H]$^+$.

Example V

Synthesis of methyl-(3aRS,4SR,11bRS)-3-allyl-2,3,3a,4,5,7-hexahydro-4-[2-ζ-1,3-dioxolan-2-yl)-4-methyloxy-1-butyl]-1H-pyrrolo[2,3-d]carbazole-6-carboxylate

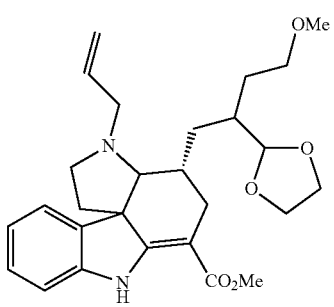 [SMILES: C=CCN1CCC23C(=C(C(=O)OC)C[C@@H](CC(CCOC)C4OCCO4)C12)Nc1ccccc13]

A mechanically stirred 3 L 3-neck round-bottomed flask was fitted with a Dean-Stark reflux apparatus, an N$_2$ bubbler, and heating mantle. To the flask was charged the indole from Example I (104.9 g, 369 mmol), 4-(1,3-dioxolan-2-yl)-6-methoxyhexanal (5, n=2, R=OMe) (89.53 g, 443 mmol), and toluene (2.4 L). The Dean-Stark trap was charged with 3 Å molecular sieves. The apparatus was flushed with nitrogen, and the mixture azeotropically refluxed for 12 hours. The mixture was cooled to room temperature and poured into hexanes (4 L) while stirring. The mixture was filtered through Celite and concentrated to give 187.9 g 6a (R=OMe, $R_1=R_2=R_3$=H, n=2) as an oil. The product was sufficiently clean to be taken directly to the next step. Yield=108%.

Example VI

Synthesis of methyl-(3aRS,4SR,11bRS)-3-(3,3-dimethylallyl)-2,3,3a,4,5,7-hexahydro-4-[2-ζ-1,3-dioxolan-2-yl)-4-methyloxy-1-butyl]-1H-pyrrolo[2,3-d]carbazole-6-carboxylate

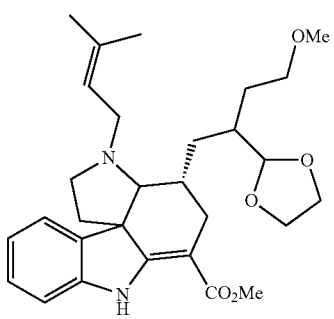 [SMILES: COCCC(C[C@@H]1CC(C(=O)OC)=C2Nc3ccccc3C23CCN(CC=C(C)C)C13)C1OCCO1]

A 500 mL round bottom flask was charged with prenylazepine (12.8 g, 40.97 mmol), toluene (250 mL), and aldehyde (crude aldehyde of ~50% purity; ca. 21.5 g, 41 mmol), and a condenser. The reaction mixture was heated to a gentle reflux and stirred 15 hours, at which time the solution was concentrated under reduced pressure and filtered through a column of silica gel (120 g) with and EtOAc/Hexane eluent. The title compound was isolated with substantial amounts of components of the crude aldehyde starting material as an oil (34.21 g). TLC (EtOAc/Hexanes, 1:1): $R_f$=0.4; ESI-MS: m/z calculated for $C_{29}H_{41}N_2O_5$, 497.30, found 497.3 [M+H]$^+$.

N.B., The later column fractions provided material potentially sufficient for NMR analysis: $^1$H NMR (400 MHz, CDCl$_3$): δ 0.68-1.44 (m, 5H), 1.61-1.73 (m, 3H), 1.74 (s, 3H), 1.78 (s, 3H), 1.96-2.10 (m, 2H), 2.39-2.48 (m, 1H), 2.52-2.76 (m, 2H), 2.82 (d, J=8.0 Hz, 1H), 3.04 (dd, J=6.0, 8.0 Hz, 1H), 3.13 (s, 1.5H), 3.16-3.36 (m, 5H), 3.43-3.54 (m, 1H), 3.58-3.89 (m, 7H), 4.64 (d, J=4.0 Hz, 0.5H), 4.70 (d, J=4.0 Hz, 0.5H), 5.39-5.48 (m, 1H), 6.81 (dd, J=2.0, 8.0 Hz, 1H), 6.83-6.91 (m, 1H), 7.10-7.19 (m, 2H), 8.93-9.05 (m, 1H).

Example VII

Synthesis of 3-allyl-1,2,3,4,5,6,7,8-octahydro-5β-[2-ζ-(1,3-dioxolan-2-yl)-4-methyloxy-1-butyl]azonino[5,4-b]indole-7-carboxylate

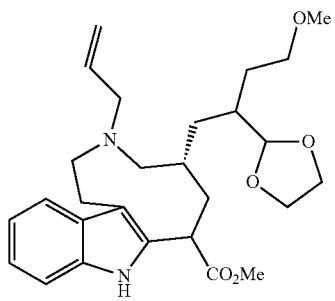 [SMILES: C=CCN1CCc2c([nH]c3ccccc23)C(C(=O)OC)C[C@@H](CC(CCOC)C2OCCO2)C1]

A 2 liter 3 neck round-bottomed flask was set up with a mechanical stirrer, temperature-controlled oil bath and reflux condenser. The compound obtained from Example V (R=OMe, $R_1=R_2=R_3$=H, n=2) (172.91 g, 369 mmol) and glacial acetic acid (738 mL) were charged to the flask, and the mixture brought to 90° C. Sodium borohydride (41.88 g, 1.11 mol) was added in small portions at such a rate as to control the ensuing reaction. After the addition was complete, the reaction mixture was poured over ice and quenched with saturated ammonium hydroxide. (Alternately, approximately ⅔ of the glacial acetic acid may be removed under reduced pressure prior to pouring on ice and making basic with ammonium hydroxide. This significantly reduces the amount of ammonium hydroxide required.) The aqueous mixture was extracted with ether several times, the extracts dried over sodium sulfate, filtered and concentrated in vacuo to give 165.2 g of the titled compound as an oil. Yield=95%.

Example VIII

Synthesis of 3-(3,3-dimethylallyl)-1,2,3,4,5,6,7,8-octahydro-5β-[2-ζ-(1,3-dioxolan-2-yl)-4-methyloxy-1-butyl]azonino[5,4-b]indole-7-carboxylate

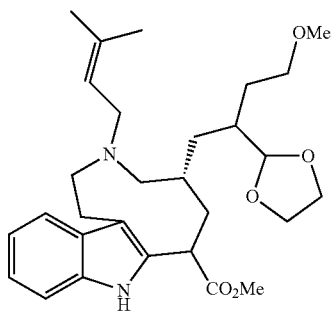 [SMILES: COCCC(C[C@@H]1CC(C(=O)OC)c2[nH]c3ccccc3c2CCN(CC=C(C)C)C1)C1OCCO1]

A 1 L round bottom flask was charged with crude α,β unsaturated ester (33 g,<40 mmol), glacial acetic acid (250 mL), and heated to 80° C. in an oil bath. NaBH$_4$ (7.6 g, 201 mmol) was added portion wise (100-500 mg portions) to the hot reaction mixture over 33 minutes. After stirring an additional 13 minutes, NaBH$_4$ (3.8 g, 100.5 mmol) was added portion wise (100-500 mg portions) over 5 minutes. After stirring an additional 15 minutes, NaBH$_4$ (3.8 g, 100.5 mmol) was added portion wise (100-500 mg portions) over 5 minutes. After stirring an additional 15 minutes, NaBH$_4$ (3.8 g, 100.5 mmol) was added portion wise (100-500 mg portions) over 5 minutes. After stirring an additional 15 minutes, NaBH$_4$ (3.8 g, 100.5 mmol) was added portion wise (100-500 mg portions) over 5 minutes. At this point 22.8 g NaBH$_4$ had been added and TLC indicated no remaining starting material. The mixture was concentrated under reduced pressure to ⅓ the original volume and diluted with isopropyl acetate (250 mL) with vigorous stirring. The reaction flask was placed in a 0° C. ice bath and concentrated NH$_4$OH (140 mL) was added at room temperature. The reaction mixture was transferred to a separatory funnel and organic layer separated, then washed sequentially with water (80 mL) and NaCl brine (80 mL), dried over sodium sulfate, and concentrated. NMR suggested the presence of unreacted starting material and the crude mixture was filtered through a 40 g silica gel plug with an EtOAc/Hexanes eluent. The desired indole was isolated as a mixture of α and β ester diastereomers (22 g contaminated with staring material α,β unsaturated ester and aldehyde condensation partner, 2:1, β:α product mixture). TLC (EtOAc/Hexanes, 1:1): R$_f$=0.7.

Without being bound to any one particular direct or multi-step convergent synthesis, provided below in an exemplary embodiment of a synthesis which utilizes novel indole derived pharmaceutical intermediates in accordance with the present invention, wherein: R, and R$_1$-R$_3$ are each independently selected from the group consisting of H, an alkyl, cycloalkyl, polycycloalkyl, heterocycloalkyl, aryl, alkaryl, aralkyl, alkoxy, alkanoyl, aroyl, alkenyl, and/or alkyl-alkenyl group containing approximately 1 to approximately 25 carbon atom(s); and n is an integer ranging from approximately 2 to approximately 5.

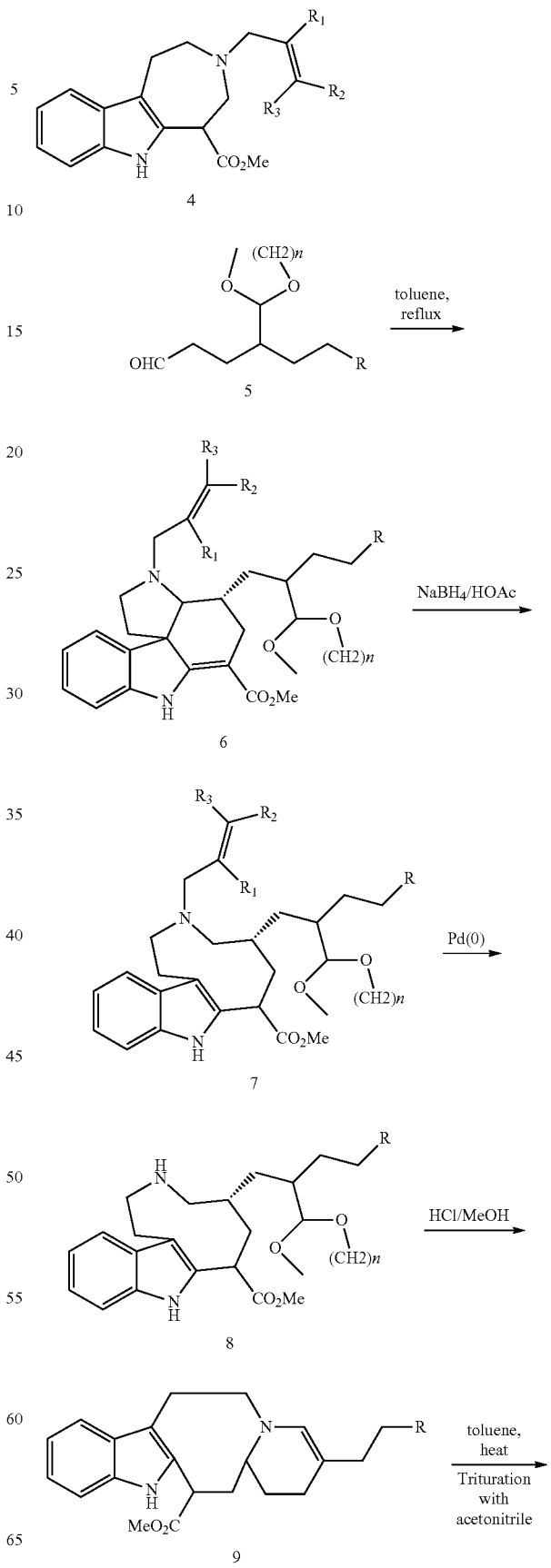

-continued

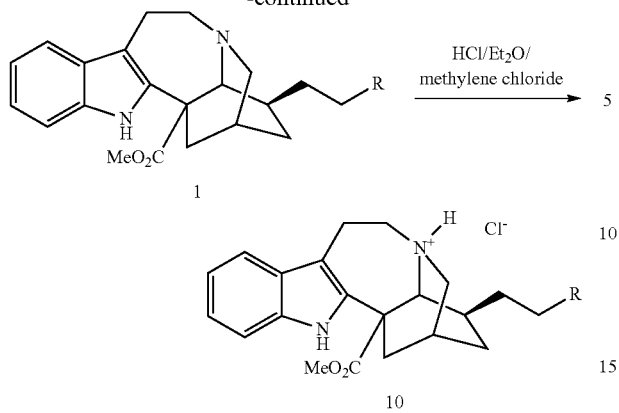

It will be understood that while a plurality of the examples provided surpa utilize allyl moieties as protecting groups, one of ordinary skill in the art having the present disclosure before them will appreciate that other protecting groups are likewise contemplated for use in accordance with the present invention including, but not limited to, alkyl groups (e.g., methyl, ethyl, t-butyl, neopentyl, adamantyl, etcetera) containing approximately 1 to approximately 25 carbon atom(s). By way example chloroformates (e.g., methyl chloroformate) are effective for removing such alkyl protecting groups. Notably, both neopentyl and adamantyl alkyl groups are void of beta hydrogen configurations, and, as such, can preclude certain degradation pathways known at beta positions.

It will be further understood that any reference to compounds disclosed herein includes pharmaceutically acceptable salts and/or solvates of the same.

The foregoing description merely explains and illustrates the invention and the invention is not limited thereto except insofar as the appended claims are so limited, as those skilled in the art who have the disclosure before them will be able to make modifications without departing from the scope of the invention.

What is claimed and desired to be secured by Letters Patent of the United States is:

1. A compound of the structure of formula VI:

(VI)

wherein:

$R_1$-$R_3$ are each independently selected from the group consisting of H, $CH_3$, and $C_6H_5$;

$R_4$ is selected from the group consisting of an alkyl, cycloalkyl, polycycloalkyl, heterocycloalkyl, aryl, alkaryl, aralkyl, alkoxy, alkanoyl, aroyl, alkenyl, and/or alkyl-alkenyl group containing 1 to 25 carbon atom(s); and n is an integer ranging from 2 to 5.

2. A compound, of comprising the structure of formula VII:

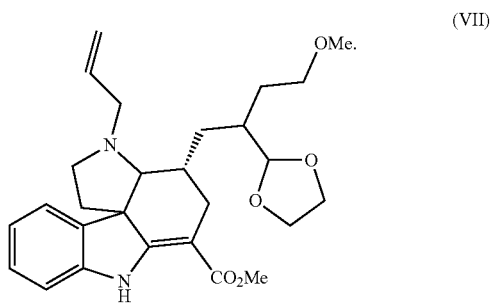 [SMILES: C=CCN1CCC23C(=C(C(=O)OC)C[C@@H](CC(CCOC)C4OCCO4)C12)Nc1ccccc13]

(VII)

3. A compound, of comprising the structure of formula VIII:

(VIII)

* * * * *